(12) United States Patent
Taya et al.

(10) Patent No.: US 8,313,933 B2
(45) Date of Patent: Nov. 20, 2012

(54) L-AMINO ACID PRODUCING BACTERIUM AND METHOD FOR PRODUCING L-AMINO ACID

(75) Inventors: Masahito Taya, Toyonaka (JP);
Motomu Nishioka, Toyonaka (JP);
Yoshihiro Ojima, Toyonaka (JP);
Mizuho Komaki, Toyonaka (JP);
Shintaro Iwatani, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 180 days.

(21) Appl. No.: 12/546,830

(22) Filed: Aug. 25, 2009

(65) Prior Publication Data

US 2010/0055748 A1    Mar. 4, 2010

Related U.S. Application Data

(60) Provisional application No. 61/154,500, filed on Feb. 23, 2009.

(30) Foreign Application Priority Data

Feb. 8, 2008  (JP) ................................ 2008-029311
Aug. 26, 2008  (JP) ................................ 2008-216425

(51) Int. Cl.
*C12P 13/24*   (2006.01)
*C12P 13/22*   (2006.01)
*C12P 13/20*   (2006.01)
*C12P 13/16*   (2006.01)
*C12P 13/14*   (2006.01)
*C12P 13/10*   (2006.01)
*C12P 13/08*   (2006.01)
*C12P 13/06*   (2006.01)
*C12N 1/20*    (2006.01)
*C12N 1/21*    (2006.01)
*C07H 21/02*   (2006.01)
*C07H 21/04*   (2006.01)

(52) U.S. Cl. ........ 435/107; 435/108; 435/109; 435/110; 435/113; 435/114; 435/115; 435/116; 435/252.3; 435/252.33; 536/23.1; 536/23.7

(58) Field of Classification Search .......................... None
See application file for complete search history.

(56) References Cited

U.S. PATENT DOCUMENTS

| | | | |
|---|---|---|---|
| 5,175,107 A | | 12/1992 | Debabov et al. |
| 5,686,277 A | * | 11/1997 | Kim et al. ..................... 435/158 |
| 5,688,671 A | | 11/1997 | Sugimoto et al. |
| 5,932,453 A | | 8/1999 | Kikuchi et al. |
| 6,132,999 A | | 10/2000 | Debabov et al. |
| 6,303,348 B1 | | 10/2001 | Livshits et al. |
| 6,319,696 B1 | | 11/2001 | Kishino et al. |
| 7,186,531 B2 | | 3/2007 | Akhverdian et al. |
| 7,300,776 B2 | | 11/2007 | Ito et al. |
| 2002/0110876 A1 | | 8/2002 | Miyata et al. |
| 2003/0157667 A1 | | 8/2003 | Vitushkina et al. |
| 2004/0132165 A1 | | 7/2004 | Akhverdian et al. |
| 2005/0191684 A1 | | 9/2005 | Zimenkov et al. |
| 2005/0239177 A1 | | 10/2005 | Livshits et al. |
| 2006/0035348 A1 | | 2/2006 | Gulevich et al. |
| 2006/0088919 A1 | | 4/2006 | Rybak et al. |
| 2006/0216796 A1 | | 9/2006 | Hashiguchi et al. |
| 2007/0004014 A1 | | 1/2007 | Tsuji et al. |
| 2008/0009041 A1 | * | 1/2008 | Mizoguchi et al. .......... 435/71.1 |

FOREIGN PATENT DOCUMENTS

EP    0488424    6/1992

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry.*
Huang, Y., et al., "Expression and Regulation of the *yggG* Gene of *Escherichia coli*," Curr. Microbiol. 2008;56:14-20.
Huang, Y., et al., "Up-regulation of *yggG* promotes the survival of *Escherichia coli* cells containing Era-1 mutant protein," FEMS Microbiol. Lett. 2007;275:8-15.
Material presented in the 73$^{rd}$ Annual Meeting of the Society of Chemical Engineers, Japan, on Mar. 18, 2008, at Hamamatsu Campus, Shizuoka Univ., Shizuoka, Japan.
Summary of 60$^{th}$ Annual Meeting of the Society for Biotechnology, Japan, issued Jul. 11, 2008, p. 142 with an English translation.

* cited by examiner

*Primary Examiner* — Anand Desai
*Assistant Examiner* — Iqbal H Chowdhury
(74) *Attorney, Agent, or Firm* — Shelly Guest Cermak; Cermak Nakajima LLP

(57) ABSTRACT

An L-amino acid can be produced by culturing an L-amino acid-producing bacterium which belongs to the Enterobacteriaceae family and which has been modified so that the expression of a yggG gene is enhanced.

9 Claims, No Drawings

L-AMINO ACID PRODUCING BACTERIUM AND METHOD FOR PRODUCING L-AMINO ACID

This application claims priority under 35 U.S.C. §119 to Japanese Patent Application No. 2008-216425, filed on Aug. 26, 2008, and U.S. Provisional Patent Application No. 61/154,500, filed on Feb. 23, 2009, which are incorporated in their entireties by reference. The Sequence Listing in electronic format filed herewith is also hereby incorporated by reference in its entirety (File Name: US-387_Seq_List; File Size: 7 KB; Date Created: Aug. 25, 2009).

BACKGROUND OF THE INVENTION

1. Field of the Invention

The present invention relates to a method of producing an L-amino acid using a bacterium, and more particularly, to a method of producing an L-amino acid such as L-threonine and L-phenylalanine. L-threonine is useful as an additive in animal feeds, health food, amino acid infusions, and the like. L-phenylalanine is useful as a precursor for synthesizing alpha-L-aspartyl-L-phenylalanine.

2. Brief Description of the Related Art

L-amino acids are industrially produced by fermentation using various microorganisms. For example, L-glutamic acid is typically produced by fermentation utilizing the so-called coryneform bacteria, which belong to the genus *Brevibacterium, Corynebacterium* or *Microbacterium*, or mutant strains thereof (Kunihiko Akashi et al., "Amino acid fermentation", pp. 195-215, 1986, Japan Scientific Societies Press). Methods for producing L-glutamic acid by fermentation using other bacterial strains include methods using a microorganism belonging to the genus *Bacillus, Streptomyces, Penicillium* or the like (U.S. Pat. No. 3,220,929), methods using a microorganism belonging to the genus *Pseudomonas, Arthrobacter, Serratia, Candida* or the like (U.S. Pat. No. 3,563,857), methods using a microorganism belonging to the genus *Bacillus, Pseudomonas, Serratia, Aerobacter aerogenes* (currently referred to as *Enterobacter aerogenes*) or the like (Japanese Patent Publication (KOKOKU) No. 32-9393), methods using a mutant strain of *Escherichia coli* (Japanese Patent Laid-open (KOKAI) No. 5-244970), and so forth. In addition, methods for producing L-glutamic acid using a microorganism belonging to the genus *Klebsiella, Erwinia, Pantoea* or *Enterobacter* have also been disclosed (Japanese Patent Laid-open Nos. 2000-106869, 2000-189169, and 2000-189175).

Methods for producing a target substance such as L-amino acid using such bacteria include methods using wild-type bacteria, methods using nutrient-auxotrophic mutants derived from wild-type bacteria, methods using metabolic regulation mutants derived from wild-type bacteria, and methods using mutants that have properties of a nutrient auxotrophic mutant and a metabolic regulation mutant.

Recently, DNA recombination techniques have been used for fermentative production of target substances. For example, L-amino acid productivity was improved by enhancing expression of genes encoding L-amino acid biosynthetic enzymes (U.S. Pat. No. 5,168,056 and U.S. Pat. No. 5,776,736), or by enhancing carbon influx into L-amino acid biosynthetic pathway (U.S. Pat. No. 5,906,925).

Huang Y et al. (FEMS Microbiol Lett 275 (2007) 8-15) reported that the yggG gene encodes a membrane-localized heat-shock protein with a molecular weight of about 25 kDa. This protein is predicted to be a metallopeptidase based on its sequence information, and that the yggG gene product interacts with a Era protein, which is GTPase. Huang Y et al. also reported that expression of the yggG gene is increased in an era-mutant strain and era-overexpressing strain (Curr Microbiol. 2008 January; 56(1):14-20. Epub 2007 October 2). However, the physiological function of the yggG gene is unknown and there have been no reports on the relationship between enhancing yggG gene expression and L-amino acid production.

SUMMARY OF THE INVENTION

An aspect of the present invention is to provide a bacterium belonging to the Enterobacteriaceae family which is capable of effectively producing an L-amino acid and a method of effectively producing an L-amino acid using the bacterium.

The inventors of the present invention have made extensive studies to achieve the above-mentioned aspect. As a result, they have found that production of an L-amino acid can be improved by modifying a bacterium to enhance the expression of the yggG gene.

That is, the present invention is as follows.

It is an aspect of the present invention to provide an L-amino acid-producing bacterium belonging to the Enterobacteriaceae family, which has been modified so that expression of yggG gene can be enhanced.

It is another aspect of the present invention to provide the bacterium as described above, wherein expression of yggG gene can be enhanced by a method selected from the group consisting of:

a) increasing the copy number of the yggG gene, and b) modifying an expression regulatory sequence of said gene.

It is another aspect of the present invention to provide the bacterium as described above, wherein the yggG gene is selected from the group consisting of:

(A) a DNA that encodes a protein comprising the amino acid sequence of SEQ ID NO: 2; and (B) a DNA that encodes a protein comprising the amino acid sequence of SEQ ID NO: 2 but which includes substitutions, deletions, insertions or additions of one or several amino acids, and wherein said DNA enhances L-amino acid producing ability of a host bacterium when it is introduced into the host bacterium.

It is another aspect of the present invention to provide the bacterium as described above, wherein said yggG gene is selected from the group consisting of:

(a) a DNA comprising the nucleotide sequence of SEQ ID NO: 1, and (b) a DNA that hybridizes with the nucleotide sequence which is complementary to SEQ ID NO: 1, or with a probe that is prepared from the nucleotide sequence under stringent conditions, and wherein said DNA enhances L-amino acid producing ability of a host bacterium when it is introduced into the host bacterium.

It is another aspect of the present invention to provide the bacterium as described above, wherein the bacterium belongs to the genus *Escherichia, Pantoea*, or *Enterobacter*.

It is another aspect of the present invention to provide the bacterium as described above, wherein the bacterium belongs to the genus *Escherichia*.

It is another aspect of the present invention to provide the bacterium as described above, wherein the bacterium is *Escherichia coli*.

It is another aspect of the present invention to provide a method of producing an L-amino acid comprising culturing the bacterium as described above in a medium, and collecting the L-amino acid from the medium or the bacterium.

It is another aspect of the presently disclosed subject matter to provide the method as described above, wherein the L-amino acid can be selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

It is another aspect of the present invention to provide the method as described above, wherein the L-amino acid is selected from the group consisting of aromatic L-amino acids and L-threonine.

By using an exemplary bacterium of the present invention, L-amino acids such as L-glutamic acid, L-lysine, L-threonine, L-arginine, L-histidine, L-isoleucine, L-valine, L-leucine, L-phenylalanine, L-tyrosine, L-tryptophan, and L-cysteine can be efficiently produced.

DETAILED DESCRIPTION OF EXEMPLARY EMBODIMENTS

Hereinafter, the presently disclosed subject matter will be described in detail.

<1> Exemplary Bacteria in Accordance with the Presently Disclosed Subject Matter Exemplary bacteria in accordance with the presently disclosed subject matter can belong to the Enterobacteriaceae family, and can have an L-amino acid-producing ability, and can be modified so that the expression of a yggG gene can be enhanced. Herein, the term "L-amino acid-producing ability" refers to the ability to produce and accumulate an L-amino acid in a medium at a collectable level when exemplary bacteria in accordance with the presently disclosed subject matter are cultured in the medium. Bacteria in accordance with the presently disclosed subject matter may be able to produce a plurality of L-amino acids. The L-amino acid-producing ability can be native to the bacterium, or can be obtained by modifying the bacterium as shown below to impart the L-amino acid-producing ability by mutation or a recombinant DNA technique.

The kind of L-amino acid is not particularly limited, and examples thereof can include the basic L-amino acids such as L-lysine, L-ornithine, L-arginine, L-histidine and L-citrulline; the aliphatic L-amino acids such as L-isoleucine, L-alanine, L-valine, L-leucine, and L-glycine; the hydroxy monoaminocarboxylic acids such as L-threonine and L-serine; the cyclic L-amino acids such as L-proline; the aromatic L-amino acids such as L-phenylalanine, L-tyrosine, and L-tryptophan; the sulfur-containing L-amino acids such as L-cysteine, L-cystine, and L-methionine; and the acidic L-amino acids such as L-glutamic acid, L-aspartic acid, L-glutamine, and L-asparagine. Among them, L-threonine and aromatic L-amino acids such as L-phenylalanine, L-tyrosine, and L-tryptophan are exemplary. Exemplary bacteria in accordance with the presently disclosed subject matter may be able to produce two or more kinds of amino acids.

<1-1> Imparting L-Amino Acid-Producing Ability

Hereinafter, methods of imparting the L-amino acid-producing ability will be described, as well as examples of the bacteria to which an L-amino acid-producing ability has been imparted. However, the bacterium is not limited thereto, as long as it has an L-amino acid-producing ability.

Bacteria to be used in accordance with the presently disclosed subject matter are not particularly limited as long as they belong to Enterobacteriaceae family such as *Escherichia* bacterium, *Enterobacter* bacterium, *Pantoea* bacterium, *Klebsiella* bacterium, *Serratia* bacterium, *Erwinia* bacterium, *Salmonella* bacterium, and *Morganella* bacterium, and have L-amino acid producing ability. Specifically, those classified into the Enterobacteriaceae family according to the taxonomy used in the NCBI (National Center for Biotechnology Information) database (http://www.ncbi.nlm.nih.gov/Taxonomy/Browser/wwwtax.cgi?id=91347) can be used. As an exemplary parent strain of the Enterobacteriaceae family which can be used to perform the modification, a bacterium of the genus *Escherichia, Enterobacter, Pantoea, Erwinia*, or *Klebsiella* can be used.

Bacteria to be used in accordance with the presently disclosed subject matter are not particularly limited as long as they belong to Enterobacteriaceae family such as *Escherichia* bacterium, *Enterobacter* bacterium, *Pantoea* bacterium, *Klebsiella* bacterium, *Serratia* bacterium, *Erwinia* bacterium, *Salmonella* bacterium, and *Morganella* bacterium, and have L-amino acid producing ability. Specifically, those classified into the Enterobacteriaceae family according to the taxonomy used in the NCBI (National Center for Biotechnology Information) database (www.ncbi.nlm.nih.gov/Taxonomy/Browser/wwwtax.cgi?id=91347) can be used. As an exemplary parent strain of the Enterobacteriaceae family which can be used to perform the modification, a bacterium of the genus *Escherichia, Enterobacter, Pantoea, Erwinia*, or *Klebsiella* can be used.

These strains are available from, for example, the American Type Culture Collection (Address: 12301 Parklawn Drive, Rockville, Md. 20852, P.O. Box 1549, Manassas, Va. 20108, United States of America). That is, registration numbers are given to each of the strains, and the strains can be ordered by using these registration numbers (refer to www.atcc.org/). The registration numbers of the strains are listed in the catalogue of the American Type Culture Collection.

Examples of the *Enterobacter* bacteria can include *Enterobacter agglomerans, Enterobacter aerogenes* and so forth, and examples of the *Pantoea* bacteria can include *Pantoea ananatis*. Some strains of *Enterobacter agglomerans* were recently reclassified into *Pantoea agglomerans, Pantoea ananatis*, or *Pantoea stewartii* on the basis of the nucleotide sequence analysis of 16S rRNA etc. A bacterium belonging to either *Enterobacter* or *Pantoea* can be used so long as it is classified as the Enterobacteriaceae family.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea stewartii* (International Journal of Systematic Bacteriology, January 1993, 43:162-173).

Examples of the *Enterobacter* bacteria can include, but are not limited to, *Enterobacter agglomerans, Enterobacter aerogenes*, and so forth. Specifically, the strains exemplified in European Patent Publication No. 952221 can be used.

A typical strain of the genus *Enterobacter* can be the *Enterobacter agglomerans* ATCC 12287 strain.

Examples of the *Pantoea* bacteria can include, but are not limited to, *Pantoea ananatis, Pantoea stewartii, Pantoea agglomerans*, and *Pantoea citrea*. Specifically, the following strains can be exemplary:

*Pantoea ananatis* AJ13355 strain (FERM BP-6614) (EP0952221A);

Pantoea ananatis AJ13356 strain (FERM BP-6615) (EP0952221A); and

Pantoea ananatis AJ13601 strain (FERM BP-7207) (EP0952221A).

These strains were identified as *Enterobacter agglomerans* when they were isolated and deposited as the *Enterobacter agglomerans*. However, they were recently reclassified as *Pantoea ananatis* on the basis of nucleotide sequencing of 16S rRNA and so forth.

Examples of the *Erwinia* bacteria can include, but are not limited to, *Erwinia amylovora* and *Erwinia carotovora*, and examples of the *Klebsiella* bacteria can include *Klebsiella planticola*. Specific examples of *Erwinia* bacteria and *Klebsiella* bacteria can include the following:

Erwinia amylovora ATCC15580 strain;

Erwinia carotovora ATCC15713 strain;

Klebsiella planticola AJ13399 strain (FERM BP-6600) (EP955368A); and

Klebsiella planticola AJ13410 strain (FERM BP-6617) (EP955368A).

Hereinafter, methods to impart L-amino acid-producing ability to bacteria of the Enterobacteriaceae family and methods to enhance L-amino acid-producing ability in the bacteria will be described.

In order to impart the L-amino acid-producing ability, methods can be used which are used in conventional breeding of *Escherichia* bacteria or the like, such as by acquiring nutrient-auxotrophic mutant strains, analogue resistant strains, or metabolic regulation mutant strains, or by creating recombinant strains having enhanced expression of L-amino acid biosynthetic enzymes (Amino Acid Fermentation, Japan Scientific Societies Press, first edition publication: May 30, 1986, p. 77 to 100). In breeding an L-amino acid-producing bacterium, properties such as nutrient-auxotrophy, analogue-resistance, and metabolic regulation can be imparted alone or in combination. Furthermore, expression of one or more L-amino acid biosynthetic enzymes can be enhanced. Furthermore, imparting of such properties as nutrient-auxotrophy, analogue-resistance and metabolic regulation mutation can be combined with enhancing the expression of the L-amino acid biosynthetic enzymes.

Nutrient-auxotrophic mutant strains, L-amino acid-analogue resistant strains, and metabolic regulation mutant strains that have an L-amino acid-producing ability can be obtained as follows. A parent strain or a wild-type strain can be subjected to a typical mutation treatment, such as irradiation with X-rays or ultraviolet rays, or by treating with a mutagen, including N-methyl-N'-nitro-N-nitrosoguanidine (NTG) and ethylmethanesulfonate (EMS), followed by selection of the strains that exhibit nutrient-auxotrophy, analogue-resistance, or a metabolic regulation mutation and have an L-amino acid-producing ability.

Hereinafter, L-amino acid-producing bacteria and methods of constructing such bacteria will be exemplified.

L-glutamic acid-producing bacteria

L-glutamic acid-producing bacteria are exemplified.

Examples of parent strains which can be used to derive L-glutamic acid-producing bacteria in accordance with the presently disclosed subject matter can include, but are not limited to, strains belonging to the genus *Escherichia*, such as *E. coli* VL334thrC$^+$ (EP 1172433). *E. coli* VL334 (VKPM B-1641) is auxotrophic for L-isoleucine and L-threonine and is mutated in the thrC and ilvA genes (U.S. Pat. No. 4,278, 765). A wild-type allele of the thrC gene was transferred by general transduction using a bacteriophage P1 grown on the wild-type *E. coli* strain K12 (VKPM B-7). As a result, an L-isoleucine auxotrophic strain VL334thrC$^+$ (VKPM B-8961) was obtained.

Methods to impart L-glutamic acid-producing ability to bacteria or methods to enhance L-glutamic acid-producing ability in the bacteria can include methods of modifying bacteria to enhance expression of genes encoding enzymes involved in L-glutamic acid biosynthesis.

Examples of the enzymes involved in L-glutamic acid biosynthesis can include glutamate dehydrogenase (hereinafter, also referred to as GDH) (gdhA), glutamine synthetase (glnA), glutamate synthetase (gltAB), isocitrate dehydrogenase (icdA), aconitate hydratase (acnA, acnB), citrate synthase (hereinafter, also referred to as CS) (gltA), methylcitrate synthase (hereinafter, also referred to as PRPC) (prpC), phosphoenolpyruvate carboxylase (hereinafter, also referred to as PEPC) (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi). Terms in parentheses show gene names (also in the descriptions below). Among these enzymes, by way of example, at least one of CS (or PRPC), PEPC and GDH can be used. In another example, all three enzymes can be used (WO2006/051660).

Hereinafter, methods of modifying bacteria to enhance the expression of target genes will be exemplified.

An exemplary method in accordance with the presently disclosed subject matter can involve increasing the copy number of an objective gene. For example, the objective gene can be cloned into an appropriate plasmid, and the plasmid used to transform a host bacterium. For example, when the gene encoding CS (gltA), the gene encoding PRPC (prpC), the gene encoding PEPC (ppc), or the gene encoding GDH (gdhA) is the objective gene, the nucleotide sequences of these genes from *Escherichia* bacteria and *Corynebacterium* bacteria have been reported (Biochemistry, vol. 22, pp. 5243-5249, 1983; J. Biochem., vol. 95, pp. 909-916, 1984; Gene, vol. 27, pp. 193-199, 1984; Microbiology, vol. 140, pp. 1817-1828, 1994; Mol. Gen. Genet., vol. 218, pp. 330-339, 1989; Molecular Microbiology, vol. 6, pp. 317-326, 1992); and therefore, these genes can be obtained by synthesizing primers based on their respective nucleotide sequences, and performing PCR using the chromosomal DNA of bacteria belonging to the family Enterobacteriaceae as a template.

Examples of a plasmid that can be used for transformation can include those which are autonomously replicable in bacteria of the Enterobacteriaceae family such as pUC19, pUC18, pHSG299, pHSG399, pHSG398, pACYC184, (pHSG and pACYC are available from Takara Bio Inc.), RSF1010 (Gene vol. 75(2), p271-288, 1989), pBR322, pMW219, pMW119 (pMW is available form Nippon Gene Co., Ltd.), pSTV28, and pSTV29 (Takara Bio Inc.). A phage DNA vector can also be used. Examples of a plasmid for enhancing activities of the aforementioned CS or PRPC, PEPC and GDH simultaneously can include RSPCPG (EP0952221A) into which gltA gene, ppc gene and gdhA gene are introduced, and RSPPPG where gltA gene of RSFCPG is replaced by prpC.

Examples of transformation methods can include treating recipient cells with calcium chloride so to increase permeability of the DNA, which has been reported for *Escherichia coli* K-12 (Mandel, M. and Higa, A., 1970, J. Mol. Biol., 53:159), and preparing competent cells from cells which are at the growth phase, followed by transformation with DNA, which has been reported for *Bacillus subtilis* (Duncan, C. H., Wilson, G. A. and Young, F. E. 1977, Gene, 1:153). Alternatively, a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts (Chang, S, and Choen, S. N., 1979, Mol. Gen. Genet., 168:111; Bibb, M. J. et al., 1978, Nature, 274:398; Hinnen, A., Hicks, J. B. and Fink, G. R. 1978, Proc. Natl. Sci., USA, 75:1929) can also be employed. In addition, microorganisms can also be transformed by the electric pulse method (Japanese Patent Laid-open No. 2-207791).

The copy number of a gene can also be increased by introducing multiple copies of the gene into the chromosomal DNA of the host bacterium. Introducing multiple copies of the gene into the chromosomal DNA of the host bacterium can be attained by homologous recombination (Experiments in Molecular Genetics, Cold Spring Harbor Lab. (1972)) using a target sequence present on the chromosomal DNA in multiple copies. This can be a repetitive DNA or an inverted repeat present on the end of a transposing element. Alternatively, as disclosed in JP 2-109985 A, multiple copies of the yggG gene can be introduced into the chromosomal DNA by inserting the gene into a transposon, and transferring it so that multiple copies of the gene are integrated into the chromosomal DNA.

Furthermore, expression of a target gene can be enhanced by substituting an expression regulatory sequence such as the native promoter with a stronger promoter, whether the gene is present on the chromosome or a plasmid. Examples of known strong promoters can include the lac promoter, trp promoter, trc promoter, PR promoter and lacUV promoter. As described in WO 00/18935, several nucleotides in a promoter region can be replaced so that the promoter becomes more potent. A method to evaluate the strength of a promoter and examples of strong promoters are described in Goldstein et al. (Prokaryotic promoters in biotechnology. Biotechnol. Annu. Rev., 1995, 1, 105-128) or the like.

For example, replacement of an expression regulatory sequence can be performed in the same way as the gene replacement using a temperature-sensitive plasmid. A vector having a temperature-sensitive replication origin which can be used for obtaining exemplary bacteria of the Enterobacteriaceae family in accordance with the presently disclosed subject matter can include the pMAN997 plasmid described in WO99/03988, etc.

In addition, it is known that a spacer sequence between the ribosome binding site (RBS) and the translation initiation codon, especially, several nucleotides just upstream of the initiation codon, has a great influence on translation efficiency. Therefore, this sequence can be modified.

Modification of an expression regulatory sequence of a gene can be combined with the increase in the copy number of the gene.

Examples of a method of gene substitution can include the method using a linear DNA called "Red-driven integration" (Datsenko, K. A, and Wanner, B. L. Proc. Natl. Acad. Sci. USA. 97: 6640-6645 (2000), a combination of Red-driven integration and a cleavage system derived from λ phage (Cho, E. H., Gumport, R. I., Gardner, J. F. J. Bacteriol. 184: 5200-5203 (2002)) (WO 2005/010175), methods using a plasmid containing a temperature-sensitive replication origin, a plasmid capable of conjugation transfer, or a suicide vector which does not have a replication origin in a host cell (U.S. Pat. No. 6,303,383; JP 05-007491 A), and the like.

For example, a strain that is resistant to λ Red gene product, such as the *Pantoea ananatis* SC17(0) strain can be used for Red-driven integration. The SC17(0) strain was deposited in the Russian National Collection of Industrial Microorganisms (VKPM) (Russia, 117545 Moscow 1, Dorozhny proezd. 1) on Sep. 21, 2005 under the accession number VKPM B-9246.

Bacteria which is modified to enhance the expression of citrate synthase gene, methylcitrate synthase gene, phosphoenolpyruvate carboxylase gene and/or glutamate dehydrogenase gene by the methods as described above can include those described in JP2001-333769, JP2000-106869, JP2000-189169, JP2000-333769, JP2006-129840, and WO2006/051660.

L-glutamic acid producing ability can also be imparted by enhancing the activity or activities of either or both of 6-phosphogluconate dehydratase and 2-keto-3-deoxy-6-phosphogluconate aldorase. An example of a bacterium in which activities of 6-phosphogluconate dehydratase and 2-keto-3-deoxy-6-phosphogluconate aldorase are enhanced can include that disclosed in JP2003-274988.

Examples of parent strains which can be used to derive the L-glutamic acid-producing bacteria in accordance with the presently disclosed subject matter also can include strains which have a decreased or eliminated activity of an enzyme that catalyzes synthesis of a compound other than L-glutamic acid, and branches off from the L-glutamic acid biosynthesis pathway. Examples of such enzymes can include 2-oxoglutarate dehydrogenase (α-ketoglutarate dehydrogenase) (sucA), isocitrate lyase (aceA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and 1-pyrroline-5-carboxylate dehydrogenase (putA). Among them, 2-oxoglutarate dehydrogenase activity can be decreased or eliminated.

In order to reduce or eliminate the activities of the aforementioned enzymes, mutations can be introduced into the genes of the aforementioned enzymes by typical mutagenesis or genetic engineering techniques. Mutagenesis treatments can include, for example, irradiation with X-rays or ultraviolet rays, or treatment with a mutagenesis agent such as N-methyl-N'-nitro-N-nitrosoguanidine, and so forth. The mutation can be introduced into the coding region of the gene encoding the enzyme protein, or into a region responsible for regulating expression, such as a promoter. Genetic engineering techniques can include genetic recombination, transduction, cell fusion, and so forth.

A decrease in the intracellular activity of the objective enzyme, and the degree thereof, can be confirmed by measuring the enzyme activity in a cell extract or a purified fraction thereof obtained from the candidate strain, and comparing it with that of a wild-type strain. For example, 2-oxoglutarate dehydrogenase activity can be measured by the method of Reed et al. (Reed L. J. and Mukherjee B. B., Methods in Enzymology, 13, pp. 55-61 (1969)).

Bacteria belonging to the genus *Escherichia* deficient in the 2-oxoglutarate dehydrogenase activity or having a reduced 2-oxoglutarate dehydrogenase activity can include the following strains (U.S. Pat. Nos. 5,378,616 and 5,573,945):

*E. coli* W3110sucA:: Kmr;
*E. coli* AJ12624 (FERM BP-3853);
*E. coli* AJ12628 (FERM BP-3854);
*E. coli* AJ12949 (FERM BP-4881); and E. coli W3110sucA::Kmr is obtained by disrupting the 2-oxoglutarate dehydrogenase gene (sucA gene) of E. coli W3110. This strain is completely deficient in 2-oxoglutarate dehydrogenase.

Other strains in which 2-oxoglutarate dehydrogenase activity is deficient or decreased can include the following:

Pantoea ananatis AJ13601 (FERM BP-7207, EP1078989A);

Pantoea ananatis AJ13356 (FERM BP-6615, U.S. Pat. No. 6,331,419);

Pantoea ananatis SC17sucA (FERM BP-8646, WO2005/085419); and

Klebsiella planticola AJ13410 (FERM BP-6617, U.S. Pat. No. 6,197,559).

The SC17sucA strain was obtained from SC17 strain by disrupting 2-oxoglutarate dehydrogenase gene. The SC17 strain was obtained by selecting a low-phlegm production mutant strain from AJ13355. AJ13355strain was isolated from nature based on its ability to proliferate in a medium containing L-glutamic acid and a carbon source at low pH condition. The AJ13601 strain was obtained by introduction into the SC17sucA strain the gltA, ppc, and gdhA genes derived from Escherichia coli and the gltA gene derived from Brevibacterium lactofermentum. Then, a high concentration L-glutamic acid resistant strain at low pH was selected, and the strain having a high proliferation degree and a high L-glutamic acid producing ability was finally selected (EP0952221A). AJ13356 strain was obtained from AJ13355 strain by disrupting α-KGDH-E1 subunit gene (sucA).

AJ13355 strain and AJ13356 strain were deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under accession numbers of FERM P-16644 and FERM P-16645. They were then converted to an international deposit under the provisions of the Budapest Treaty on Jan. 11, 1999 and received an accession number of FERM BP-6614 and FERM BP-6615.

The SC17sucA strain was assigned a private number of AJ417, and it was deposited at the National Institute of Bioscience and Human-Technology, Agency of Industrial Science and Technology, Ministry of Economy, Trade and Industry (currently, the International Patent Organism Depositary, National Institute of Advanced Industrial Science and Technology, Tsukuba Central 6, 1-1, Higashi 1-Chome, Tsukuba-shi, Ibaraki-ken, 305-8566) on Feb. 26, 2004 and given an accession number of FERM BP-08646.

AJ13601 strain was deposited at the National Institute of Bioscience and Human-Technology, Agency of Industrial Science and Technology, Ministry of International Trade and Industry (currently, the International Patent Organism Depositary, National Institute of Advanced Industrial Science and Technology) on Aug. 18, 1999, and given an accession number of FERM P-17516. The deposit was then converted to an international deposit under the provisions of the Budapest Treaty on Jul. 6, 2000, and given an accession number of FERM BP-7207.

The above-mentioned Pantoea ananatis AJ13355 strain, Pantoea ananatis AJ13601 strain, Pantoea ananatis AJ13356 strain, and Klebsiella planticola AJ13410 strain have an ability to accumulate L-glutamic acid in such an amount that exceeds the saturation concentration of L-glutamic acid in the medium when they are cultured under acidic conditions.

L-glutamic acid producing ability of a bacterium of the Enterobacteriaceae family can be enhanced by making an arcA gene deficient (U.S. Pat. No. 7,090,998) or by amplifying a yhfK gene which exports L-glutamic acid (WO2005/085419).

The above-mentioned method to enhance or eliminate enzymatic activity can be applied to the bacteria that produce other L-amino acids in a similar manner.

L-threonine-Producing Bacteria

Examples of parent strains which can be used to derive the L-threonine-producing bacteria in accordance with the presently disclosed subject matter can include, but are not limited to, strains belonging to the genus Escherichia, such as E. coli TDH-6/pVIC40 (VKPM B-3996) (U.S. Pat. No. 5,175,107, U.S. Pat. No. 5,705,371), E. coli 472T23/pYN7 (ATCC 98081) (U.S. Pat. No. 5,631,157), E. coli NRRL-21593 (U.S. Pat. No. 5,939,307), E. coli FERM BP-3756 (U.S. Pat. No. 5,474,918), E. coli FERM BP-3519 and FERM BP-3520 (U.S. Pat. No. 5,376,538), E. coli MG442 (Gusyatiner et al., Genetika (in Russian), 14, 947-956 (1978)), E. coli VL643 and VL2055 (EP 1149911 A), and the like.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains pVIC40, which was obtained by inserting the thrA*BC operon which includes a mutant thrA gene into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. This strain was also deposited in the Russian National Collection of Industrial Microorganisms (VKPM) (Russia, 117545 Moscow 1, Dorozhny proezd. 1) on Apr. 7, 1987 under the accession number B-3996.

E. coli VKPM B-5318 (EP 0593792B) also can be used to derive L-threonine-producing bacteria. The B-5318 strain is prototrophic with regard to isoleucine, and a temperature-sensitive lambda-phage C1 repressor and PR promoter replaces the regulatory region of the threonine operon in plasmid pVIC40. The VKPM B-5318 strain was deposited in the Russian National Collection of Industrial Microorganisms (VKPM) on May 3, 1990 under accession number of VKPM B-5318.

Preferably, exemplary bacteria in accordance with the presently disclosed subject matter can be additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase).

The sequence of the thrA gene of Escherichia coli which encodes aspartokinase homoserine dehydrogenase I has been identified (nucleotide positions 337 to 2799, GenBank accession NC_000913.2, gi: 49175990). The thrA gene is located between the thrL and thrB genes on the chromosome of E.

*coli* K-12. The nucleotide sequence of the thrB gene of *Escherichia coli* which encodes homoserine kinase has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli* which encodes threonine synthase has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes can function together as a single threonine operon. To enhance the expression of the threonine operon, the attenuator region which affects the transcription can be removed from the operon (WO2005/049808, WO2003/097839).

The mutated thrA gene which encodes feedback-resistant aspartokinase homoserine dehydrogenase I, as well as the thrB and thrC genes can be obtained as one operon from the well-known plasmid pVIC40. This plasmid is present in the threonine producing *E. coli* strain VKPM B-3996, and is described in detail in U.S. Pat. No. 5,705,371.

The rhtA gene is at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The sequence expressing a protein encoded by the ORF1 has been designated the rhtA gene (rht: resistance to homoserine and threonine). Also, the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of *E. coli* has already been elucidated (nucleotide positions 3572511 to 3571408, GenBank accession NC_000913.1, gi: 16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manner.

Also, the nucleotide sequence of the aspC gene of *E. coli* has already been elucidated (nucleotide positions 983742 to 984932, GenBank accession NC_000913.1, gi:16128895), and can be obtained by PCR. The aspC genes from other microorganisms can be obtained in a similar manner.

L-Lysine-Producing Bacteria

Examples of L-Lysine-Producing Bacteria Belonging to the Genus *Escherichia* can include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue can include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine can include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 can be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria in accordance with the presently disclosed subject matter also can include strains in which expression of one or more genes encoding an L-lysine biosynthetic enzyme are enhanced. Examples of the enzymes involved in L-lysine biosynthesis can include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria in accordance with the presently disclosed subject matter also can include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine can include homoserine dehydrogenase (WO 95/23864), lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria in accordance with the presently disclosed subject matter can include, but are not limited to, strains belonging to the genus *Escherichia*, such as *E. coli* JM15 which has been transformed with different cysE alleles coding for feedback-resistant serine acetyltransferases (U.S. Pat. No. 6,218,168, Russian patent application 2003121601), *E. coli* W3110 which over-expresses genes which encode proteins suitable for secreting toxic substances (U.S. Pat. No. 5,972,663), *E. coli* strains with decreased cysteine desulfohydrase activity (JP11155571A2); *E. coli* W3110 with increased activity of a positive transcriptional regulator for the cysteine regulon encoded by the cysB gene (WO01/27307A1), and the like.

L-Leucine-Producing Bacteria

Examples of parent strains which can be used to derive L-leucine-producing bacteria in accordance with the presently disclosed subject matter can include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5, 5-trifluoroleucine (JP 62-34397 B and JP 8-70879 A); *E. coli* strains obtained by the genetic engineering method described in WO96/06926; *E. coli* H-9068 (JP 8-70879 A), and the like.

Bacteria in accordance with the presently disclosed subject matter can be improved by enhancing the expression of one or more genes involved in L-leucine biosynthesis. Examples of these genes can include those of the leuABCD operon, which operon can include a leuA gene which has been mutated so that it encodes isopropylmalate synthase which is resistant to feedback inhibition by L-leucine (U.S. Pat. No. 6,403,342). In addition, bacteria in accordance with the presently disclosed subject matter can be improved by enhancing the expression of one or more genes coding for proteins which excrete L-amino acids from the bacterial cell. Examples of such genes include the b2682 and b2683 genes (ygaZH genes) (EP 1239041 A2).

L-Histidine-Producing Bacteria

Examples of parent strains which can be used to derive L-histidine-producing bacteria in accordance with the presently disclosed subject matter can include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains which can be used to derive L-histidine-producing bacteria in accordance with the presently disclosed subject matter also can include strains in which expression of one or more genes encoding an L-histidine biosynthetic enzyme are enhanced. Examples of these L-histidine-biosynthetic enzymes can include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore the L-histidine-producing ability can also be efficiently enhanced by introducing a mutation which induces resistance to the feedback inhibition into ATP phosphoribosyltransferase (hisG) (Russian Patent Nos. 2003677 and 2119536).

Specific examples of strains having an L-histidine-producing ability can include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Phenylalanine-Producing Bacteria

Examples of parent strains which can be used to derive L-phenylalanine-producing bacteria in accordance with the presently disclosed subject matter can include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) can be used (EP 488-424 B1). Furthermore, L-phenylalanine producing bacteria belonging to the genus *Escherichia* which have an enhanced activity of the protein encoded by the yedA gene or the yddG gene also can be used (U.S. patent applications 2003/0148473 A1 and 2003/0157667 A1).

AJ12741 strain also can be used as a parent strain. AJ12741 strain (W3110(tyrR, tyrA)/pMGAL1) was obtained by introducing plasmid pMGAL1 that contains feedback inhibition-released 3-deoxy-D-arabino-heptulosonate 7-phosphate synthase, feedback inhibition-released chorismate mutase-prephenate dehydratase and shikimate kinase into *Escherichia coli* K-12 W3110 strain where tyrR gene and tyrA gene are deleted (JP3225597B). AJ12741 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Jun. 11, 1992 under accession numbers of FERM P-13000. It was then converted to an international deposit under the provisions of the Budapest Treaty on Sep. 14, 1994 and received an accession number of FERM BP-4796.

L-Tryptophan-Producing Bacteria

Examples of parent strains which can be used to derive the L-tryptophan-producing bacteria in accordance with the presently disclosed subject matter can include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like can be used. Furthermore, L-tryptophan producing bacteria belonging to the genus *Escherichia* which have an enhanced activity of the protein encoded by the yedA gene or the yddG gene can also be used (U.S. patent applications 2003/0148473 A1 and 2003/0157667 A1).

Examples of parent strains which can be used to derive the L-tryptophan-producing bacteria in accordance with the presently disclosed subject matter also can include strains in which one or more activities of the enzymes selected from anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation which results in desensitizing the feedback inhibition can be introduced into these enzymes. Specific examples of strains having such a mutation can include an *E. coli* SV164 which harbors desensitized anthranilate synthase and a strain obtained by transforming the plasmid pGH5 into *E. coli* SV164 (WO 94/08031), which contains a serA gene which has been mutated so that it encodes feedback-desensitized phosphoglycerate dehydrogenase.

Examples of parent strains which can be used to derive the L-tryptophan-producing bacteria in accordance with the presently disclosed subject matter also can include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability can be imparted by enhancing expression of a gene which encodes tryptophan synthase, among tryptophan operons (trpBA). The tryptophan synthase consists of α and β subunits which are encoded by trpA and trpB, respectively. In addition, L-tryptophan-producing ability can be improved by enhancing expression of the isocitrate lyase-malate synthase operon (WO2005/103275).

L-Proline-Producing Bacteria

Examples of parent strains which can be used to derive L-proline-producing bacteria in accordance with the presently disclosed subject matter can include, but are not limited to, strains belonging to the genus Escherichia, such as E. coli 702ilvA (VKPM B-8012) which is deficient in the ilvA gene and is able to produce L-proline (EP 1172433).

Exemplary bacteria in accordance with the presently disclosed subject matter can be improved by enhancing the expression of one or more genes involved in L-proline biosynthesis. Examples of preferred genes for L-proline producing bacteria can include the proB gene coding for glutamate kinase which is desensitized to feedback inhibition by L-proline (U.S. DE Pat. No. 3127361). In addition, bacteria in accordance with the presently disclosed subject matter can be improved by enhancing the expression of one or more genes coding for proteins excreting L-amino acid from the bacterial cell. Such genes include the b2682 and b2683 genes (ygaZH genes) (EP1239041 A2).

Examples of bacteria belonging to the genus Escherichia which have an activity to produce L-proline can include the following E. coli strains: NRRL B-12403 and NRRL B-12404 (GB Patent 2075056), VKPM B-8012 (Russian patent application 2000124295), plasmid mutants described in U.S. DE Pat. No. 3127361, plasmid mutants described by Bloom F. R. et al (The 15th Miami winter symposium, 1983, p. 34), and the like.

L-Arginine-Producing Bacteria

Examples of parent strains which can be used to derive L-arginine-producing bacteria in accordance with the presently disclosed subject matter can include, but are not limited to, strains belonging to the genus Escherichia, such as E. coli strain 237 (VKPM B-7925) (U.S. Patent Application 2002/058315 A1) and its derivative strains harboring mutant N-acetylglutamate synthase (Russian Patent Application No. 2001112869), E. coli strain 382 (VKPM B-7926) (EPI 170358A1), an arginine-producing strain into which the argA gene encoding N-acetylglutamate synthetase is introduced (EPI 170361A1), and the like.

Examples of parent strains which can be used to derive L-arginine producing bacteria in accordance with the presently disclosed subject matter also can include strains in which expression of one or more genes encoding an L-arginine biosynthetic enzyme are enhanced. Examples of the L-arginine biosynthetic enzymes can include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains which can be used to derive L-valine-producing bacteria in accordance with the presently disclosed subject matter can include, but are not limited to, strains which have been modified to overexpress the ilvGMEDA operon (U.S. Pat. No. 5,998,178). The of the ilvGMEDA operon required for attenuation can be removed so that expression of the operon is not attenuated by the L-valine that is produced. Furthermore, the ilvA gene in the operon can be disrupted so that threonine deaminase activity is decreased.

Examples of parent strains which can be used to derive L-valine-producing bacteria in accordance with the presently disclosed subject matter also can include mutants of aminoacyl t-RNA synthetase (U.S. Pat. No. 5,658,766). For example, E. coli VL1970, which has a mutation in the ileS gene encoding isoleucine tRNA synthetase, can be used. E. coli VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking $H^+$-ATPase also can be used (WO96/06926).

L-Isoleucine-Producing Bacteria

Examples of parent strains which can be used to derive L-isoleucine producing bacteria in accordance with the presently disclosed subject matter can include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, also can be used (JP 2-458 A, FR 0356739, and U.S. Pat. No. 5,998,178).

<1-2> Modification to Enhance the Expression of yggG Gene

Exemplary bacteria in accordance with the presently disclosed subject matter can be obtained by modifying a bacterium having an L-amino acid-producing ability as described above so that expression of the yggG gene is enhanced. However, the L-amino acid-producing ability can be imparted after the bacterium is modified so that expression of the yggG gene is enhanced.

Modification to enhance the expression of yggG gene can be accomplished by enhancing the expression of an endogenous gene, by modifying an expression regulatory region such as a promoter, or by enhancing expression of an exogenous gene by introducing a plasmid containing the gene, or the like. In addition, these exemplary methods can be combined.

The phrase "modifying so that expression of the yggG gene is enhanced" means, for example, that expression of the yggG gene is increased as compared to a wild-type strain or an unmodified strain. In an exemplary embodiment in accordance with the presently disclosed subject matter the expression of the yggG gene can be increased to at least 150% per cell as compared to a wild-type strain or an unmodified strain. In another exemplary embodiment, this expression can be increased to at least 200% per cell as compared to a wild-type strain or an unmodified strain. In another exemplary embodiment, this expression can be increased to at least 300% per cell as compared to a wild-type strain or an unmodified strain. Examples of a wild-type strain belonging to the Enterobacteriaceae family which can be used as a control can include Escherichia coli MG1655 strain (ATCC No. 47076), and Pantoea ananatis AJ13335 strain (FERM BP-6615).

The increased expression can be confirmed by comparing the mRNA level of the yggG gene to that of a wild-type or unmodified strain. Methods for confirming the expression of a gene can include Northern hybridization and RT-PCR (Molecular cloning (Cold spring Harbor Laboratory Press, Cold spring Harbor (USA), 2001)).

An example of the yggG gene for use in accordance with the presently disclosed subject matter can include the yggG gene from *Escherichia coli* which comprises the nucleotide sequence of SEQ ID NO: 1. The yggG gene can be cloned from bacteria of Enterobacteriaceae family such as *Escherichia, Pantoea, Enterobacter, Klebsiella, Serratia, Erwinia,* and *Yersinia*, based on the homology to the above-described gene.

The yggG gene for use in accordance with the presently disclosed subject matter can be obtained by PCR (polymerase chain reaction; refer to White, T. J. et al., Trends Genet., 5, 185 (1989)) with primers designed based on the known nucleotide sequence of a bacterium of Enterobacteriaceae family and a template of chromosomal DNA of the bacterium. For example, a yggG gene from *Escherichia coli* can be obtained by PCR using primers of SEQ ID NOS: 3 and 4 and chromosomal DNA of *Escherichia coli* as a template. The yggG gene homologues from other microorganisms can be obtained in a similar manner.

The phrase "yggG gene homologue" means a gene, which has high structural similarity to the *E. coli* yggG gene and improves L-amino acid-producing ability of an L-amino acid-producing bacterium. The "yggG gene homologue" can include genes which encode a protein which has homology of at least 80% to the entire sequence of SEQ ID NO: 2, and improves L-amino acid-producing ability of an L-amino acid producing bacterium. Another exemplary "yggG gene homologue" can encode a protein which has a homology of at least 90%. Another exemplary "yggG gene homologue" can encode a protein which has a homology of at least 95%. And, another exemplary "yggG gene homologue" can encode a protein which has a homology of at least 97%.

The phrase "improves L-amino acid producing ability of an L-amino acid producing bacterium" means that the gene increases the amount of L-amino acid produced from an L-amino acid producing bacterium as compared to the amount prior to introduction of the gene when the gene is introduced into the L-amino acid producing bacterium. For example, a yggG gene homolog is introduced into L-threonine producing VKPM B-3996 strain or L-phenylalanine producing AJ12741 strain described in Examples below and the yggG gene-introduced strain is cultured together with a non-introduced strain and the amount of accumulated L-threonine or L-phenylalanine is measured. If the amount of L-threonine or L-phenylalanine produced by yggG gene homolog-introduced strain is increased as compared to the non-introduced strain, such yggG gene homolog can be used for breeding a bacterium in accordance with the presently disclosed subject matter.

Meanwhile, the yggG gene can be a gene that encodes a conservative variant protein having the amino acid sequence of SEQ ID NO: 2 but which includes substitution, deletion, insertion, or addition of one or several amino acids as long as it improves L-amino acid producing ability of an L-amino acid producing bacterium. In accordance with the presently disclosed subject matter, although depending on the positions in the ternary structure and types of amino acid residues in the proteins, the term "one or several" can include a an exemplary range of 1 to 20, or an exemplary range of 1 to 10, or an exemplary range of 1 to 5. Meanwhile, the above-mentioned amino acid substitution, deletion, insertion, addition, or inversion can be a naturally occurring mutation due to an individual difference, a difference of types, or the like among the bacteria harboring the yggG gene.

The above-mentioned substitution can be a conservative substitution (neutral mutation) that does not change function of the protein Examples of conservative substitutions can include substitution between aromatic amino acids such as a substitution among Phe, Trp, and Tyr; substitution between hydrophobic amino acids such as a substitution among Leu, Ile, and Val; substitution between polar amino acids such as a substitution between Gln and Asn; substitution between basic amino acids such as a substitution among Lys, Arg, and His; substitution between acidic amino acids such as a substitution between Asp and Glu; substitution between amino acids having a hydroxyl group such as a substitution between Ser and Thr. Specific examples of a conservative substitution can include substitution of Ser or Thr for Ala; substitution of Gln, His, or Lys for Arg; substitution of Glu, Gln, Lys, His, or Asp for Asn; substitution of Asn, Glu, or Gln for Asp; substitution of Ser or Ala for Cys; substitution of Asn, Glu, Lys, His, Asp, or Arg for Gln; substitution of Gly, Asn, Gln, Lys, or Asp for Glu; substitution of Pro for Gly; substitution of Asn, Lys, Gln, Arg, or Tyr for His; substitution of Leu, Met, Val, or Phe for Ile; substitution of Ile, Met, Val, or Phe for Leu; substitution of Asn, Glu, Gln, His, or Arg for Lys; substitution of Ile, Leu, Val, or Phe for Met; substitution of Trp, Tyr, Met, Ile, or Leu for Phe; substitution of Thr or Ala for Ser; substitution of Ser or Ala for Thr; substitution of Phe or Tyr for Trp; substitution of His, Phe, or Trp for Tyr; and substitution of Met, Ile, or Leu for Val.

Degeneracy of a gene is different dependent on a host bacterium, so yggG gene can be modified so that codon is suitable for a bacterium into which the yggG gene is introduced. Furthermore, N-terminal and/or C-terminal portion of the yggG gene can be extended or deleted as long as the yggG gene improves L-amino acid-producing ability of an L-amino acid producing bacterium. The length of the extension or deletion can be less than 50 amino acids in an exemplary embodiment, less than 20 amino acids in another exemplary embodiment, less than 10 amino acids in another exemplary embodiment, or less than 5 amino acids in another exemplary embodiment. That is, 5 to 50 amino acids can be extended or deleted at N-terminus and/or C-terminus.

Meanwhile, the yggG gene can be a DNA which hybridizes with the nucleotide sequence complementary to SEQ ID NO: 1, or a probe that can be prepared from the sequence under stringent conditions, as long as it improves L-amino acid-producing ability of an L-amino acid producing bacterium.

In accordance with the presently disclosed subject matter, the term "stringent conditions" refers to conditions where a so-called specific hybrid is formed and non-specific hybrid is not formed. Although these conditions may not be completely defined a numerical value, exemplary conditions can include conditions where DNAs having high homology hybridize with each other. In an exemplary embodiment, this high homology can be a homology of at least 80%, and in another embodiment, this high homology can be at least 90%. In another embodiment, this high homology can be at least 95%. In another embodiment, this high homology can be at least 97%. It is noted that DNAs having homology of less than 80% do not hybridize with each other. These specific examples can include hybridization at an exemplary salt concentration of 1×SSC, 0.1% SDS, or at an exemplary salt concentration of 0.1×SSC, 0.1% SDS, at 60° C., which are washing conditions in general Southern hybridization.

A probe can have a partial sequence of the yggG gene. Such a probe can be prepared by PCR using oligonucleotides designed based on the nucleotide sequence of the yggG gene as primers and a DNA fragment containing the yggG gene as a template, according to conventional methods. When a DNA fragment of about 300 bp is used as a probe, after hybridization under the above-mentioned conditions, washing can be performed at 50° C., 2×SSC, 0.1% SDS, once, twice or three times.

Such homolog genes of the yggG gene can be obtained by modifying the coding region in the nucleotide sequence of SEQ ID NO: 1 so that the modified gene contains substitution, deletion, insertion or addition of/at an amino acid residue at a specific site with site-specific mutagenesis. Furthermore, homolog genes also can be obtained by the conventionally known mutagenesis techniques, such as by treating the nucleotide sequence of SEQ ID NO: 1 with hydroxylamine or the like in vitro and irradiating the microorganism containing the gene with ultraviolet light, or treating the microorganism such as a bacterium of the Enterobacteriaceae family with a known mutagen such as N-methyl-N'-nitro-N-nitrosoguanidine (NTG) or ethyl methanesulfonate (EMS). Homolog genes also can be obtained by Error-prone PCR (Cadwell, R. C. PCR Meth. Appl. 2, 28 (1992)), DNA shuffling (Stemmer, W. P. Nature 370, 389 (1994)), StEP-PCR (Zhao, H. Nature Biotechnol. 16, 258 (1998)). By these methods, a mutation is artificially introduced into the yggG gene so that yggG gene having high activity can be obtained. Whether yggG homologs improve L-amino acid-producing ability of an L-amino acid producing bacterium can be confirmed by introducing the genes into a bacterium of the Enterobacteriaceae family and determining if the L-amino acid-producing ability is improved.

<2> Method of Producing L-Amino Acid

The method of producing an L-amino acid in accordance with the presently disclosed subject matter can include culturing the bacterium in accordance with the presently disclosed subject matter in a medium to produce and accumulate an L-amino acid in the medium or bacterial cells, and collecting the L-amino acid from the medium or the bacterial cells.

Conventional media, which contain a carbon source, nitrogen source, inorganic ion, and if necessary, other organic components, can be used. Either synthetic media or natural media can be used. The carbon source and the nitrogen source to be used for the medium can be any source as long as they can be utilized by a bacterium to be cultured.

Examples of the carbon source can include sugars such as glucose, glycerol, fructose, sucrose, maltose, mannose, galactose, starch hydrolysate, and molasses; and organic acids such as acetic acid and citric acid; alcohol such as ethanol can be used alone or in combination with other carbon source. Examples of the nitrogen source can include ammonia; ammonium salts such as ammonium sulfate, ammonium carbonate, ammonium chloride, ammonium phosphate, ammonium acetate; and other nitric acid salts. As organic trace nutrients, amino acid, vitamin, fatty acid, nucleic acid, and peptone containing these, casamino acid, yeast extract, and soybean hydrolysate can be used. Nutrients, such as amino acids, can be supplemented when a nutrient-auxotrophic strain is cultured.

The culture can preferably performed under aerobic conditions at a temperature of 20° C. to 45° C. and a pH of 3 to 9. Conditions such as aeration degree can be appropriately set depending on a kind and property of the L-amino acid-producing bacterium. When pH decreases during cultivation, neutralization can be performed by adding calcium carbonate or alkali such as ammonia gas. By culturing at 10 to 120 hours, for example, under such conditions, the target L-amino acid can be accumulated in a medium.

The L-amino acid can be collected from the fermentation liquid by a conventional method. L-amino acid can be collected, for example, by concentrating and crystallizing the L-amino acid after removing cells from the medium, or by an ion-exchange chromatography.

The L-amino acid-producing bacterium, especially aromatic L-amino acid-producing bacterium, can be cultured under microaerobic conditions. The term "microaerobic conditions" can mean conditions where the concentration of dissolved oxygen in the culture medium is 25% or less, in another example 20% or less, and in another example 15% or less. Furthermore, oxygen transfer coefficient (Kla) in the medium can be 100 or less, in another example 75 or less, and in another example 50 or less.

Oxygen concentration in the medium can be microaerobic throughout the culture, or for at least some part of the culture. For example, when the method includes the step of proliferating the L-amino acid-producing bacterium (growth phase) and the step of producing L-amino acid (L-amino acid production phase), the L-amino acid production phase can be performed under microaerobic conditions, and the growth phase may be performed under aerobic conditions or microaerobic conditions. Here, the "growth phase" can mean a period of within 3 hours, in another example within 6 hours, and in another example within 10 hours from the start of the culture when the carbon source is mainly consumed by cell growth, namely, when the bacterium grows logarithmically. The "L-amino acid production phase" can mean the period after the growth phase when the carbon source is mainly consumed by L-amino acid production.

By way of example, phenylalanine produced by a method in accordance with the presently disclosed subject matter can be used for producing lower alkyl ester of α-L-aspartyl-L-phenylalanine (also referred to as "aspartame"). A lower alkyl ester of α-L-aspartyl-L-phenylalanine can be produced by solubilizing a crystal of L-phenylalanine produced by a method in accordance with the presently disclosed subject matter as described above and synthesizing a lower alkyl ester of α-L-aspartyl-L-phenylalanine from the L-phenylalanine and aspartic acid or its derivative. Methyl ester, ethyl ester and propyl ester are examples of lower alkyl ester.

A process for synthesizing a lower alkyl ester of α-L-aspartyl-L-phenylalanine from L-phenylalanine and aspartic acid or its derivative is not particularly limited and any conventional method can be applied so long as L-phenylalanine or its derivative can be used for synthesis of lower alkyl ester of α-L-aspartyl-L-phenylalanine. As a specific example, a lower alkyl ester of α-L-aspartyl-L-phenylalanine can be produced by the following process (U.S. Pat. No. 3,786,039). L-phenylalanine can be esterified to obtain lower alkyl ester of L-phenylalanine. The L-phenylalanine alkyl ester can be reacted with L-aspartic acid derivative in which β-carboxyl group is protected and α-carboxyl group is activated with esterification. The derivative can include N-acyl-L-aspartic anhydride such as N-formyl-, N-carbobenzoxy-, or N-p-methoxycarbobenzoxy-L-aspartic anhydride. By the condensation reaction, a mixture of N-acyl-α-L-aspartyl-L-phenylalanine and N-acyl-β-L-aspartyl-L-phenylalanine can be obtained. When the condensation reaction is performed under in the presence of an organic acid whose acid dissociation constant at 37° C. is $10^{-4}$ or less, the ratio of α-form to β-form in the mixture can be increased (Japanese Patent Laid-Open Publication No. 51-113841). Then the N-acyl-α-L-aspartyl-L-phenylalanine can be separated from the mixture, followed by hydrogenation to obtain α-L-aspartyl-L-phenylalanine.

α-L-aspartyl-L-phenylalanine-α-ester can be produced easily and efficiently by producing α-L-aspartyl-L-phenylalanine-β-ester from L-phenylalanine and L-aspartyl-α,β-diester using an enzyme or enzyme composition that catalyzes the nucleophilic reaction of L-phenylalanine to α-ester, not β-ester of the L-aspartyl-α,β-diester, and converting the α-L-aspartyl-L-phenylalanine-β-ester to α-L-aspartyl-L-phenylalanine-α-ester (WO2004/065610).

Furthermore, α-L-aspartyl-L-phenylalanine can be produced according to a method of the presently disclosed subject matter using a mutant of dipeptide synthesizing enzyme from *Sphingobacterium* (WO2006/075486).

EXAMPLES

Hereinafter, the presently disclosed subject matter will be described in more detail by referring to the following non-limiting examples.

Cloning of *E. coli* yggG gene and construction of an expression plasmid for yggG gene

```
Primers
Forward
5'→3' GCTCTAGAGATGAAAATTCGCG 22 bp   (SEQ ID NO: 3)

Reverse
5'→3' CGGAATTCTTACTTAATCCCATC 23 bp  (SEQ ID NO: 4)
```

These primers were used to perform PCR using the chromosomal DNA of *Escherichia coli* MM294 strain as a template and KOD plus DNA polymerase (TOYOBO) to amplify a DNA fragment of about 0.8 kbp. PCR conditions were 30 cycles of 94° C. for 2 minutes, 55° C. for 1.5 minutes and 68° C. for 1.5 minutes.

The amplified DNA fragment was purified by agarose gel electrophoresis and extracted from the gel by DNA extraction kit (QIAGEN). The DNA fragment was digested with XbaI and EcoRI, and then ligated to XbaI and EcoRI-digested vector, pHSG299 (Takara Bio) with DNA Ligation Kit (Nippon Gene). *E. coli* DH5α strain was transformed with the ligation product and the plasmid for amplifying the yggG gene (pHSG299-yggG) was obtained from the transformant.

Example 1

Construction of L-Phenylalanine Producing Strain in which yggG Gene is Overexpressed and Production of L-Phenylalanine L-phenylalanine producing *Escherichia coli* AJ12741 strain (FERM BP-4796) was transformed with the pHSG299-yggG to obtain AJ12741/pHSG299-yggG strain.

1 loop each of glycerol stock of the AJ12741/pHSG299-yggG strain and AJ12741 strain (control) was applied on an LB-agarose plate (1% Trypton, 0.5% yeast extract, 1% NaCl, and 1.5% agarose), and a resting culture was performed at 37° C. for 24 hours. 1 loop (about 10 μl) of the bacterial cells on the plate was inoculated into 40 mL of the fermentation medium described below in a 200-mL Sakaguchi flask, and culture was performed at 37° C. with shaking.

L-phenylalanine production medium for *Escherichia* bacteria:

| | |
|---|---|
| Glucose | 40 g/L |
| KH$_2$PO$_4$ | 1 g/L |
| (NH$_4$)$_2$SO$_4$ | 16 g/L |
| MgSO$_4$ | 1 g/L |
| FeSO$_4$ | 10 mg/L |
| MnSO$_4$ | 8 mg/L |
| Yeast extract | 2 g/L |
| CaCO$_3$ | 20 g/L |

After glucose was completely consumed, the amounts of L-phenylalanine which accumulated in the medium were determined. As a result, it was found that L-phenylalanine production was improved in the yggG gene-amplified strain.

TABLE 1

L-phenylalanine production

| Strain name | Concentration of L-phenylalanine (g/L) | Yield (%) |
|---|---|---|
| AJ12741 | 3.6 | 9.4 |
| AJ12741/pHSG299-yggG | 7.6 | 19.3 |

Example 2

Construction of L-Threonine Producing Strain in which yggG Gene is Overexpressed and Production of L-Threonine L-threonine producing *Escherichia coli* VKPM B-3996 strain (B-3996) was transformed with the pHSG299-yggG to obtain B-3996/pHSG299-yggG strain.

1 loop each of glycerol stock of the B-3996/pHSG299-yggG strain and B-3996 strain (control) was applied on an LB-agarose plate (1% Trypton, 0.5% yeast extract, 1% NaCl, and 1.5% agarose), and a resting culture was performed at 37° C. for 24 hours. 1 loop (about 10 μl) of the bacterial cells on the plate was inoculated into 40 mL of the fermentation medium described below in a 200-mL Sakaguchi flask, and culture was performed at 40° C. with shaking.

L-threonine production medium for *Escherichia* bacteria:

| | |
|---|---|
| Glucose | 40 g/L |
| KH$_2$PO$_4$ | 1 g/L |
| (NH$_4$)$_2$SO$_4$ | 16 g/L |
| MgSO$_4$ | 1 g/L |
| FeSO$_4$ | 10 mg/L |
| MnSO$_4$ | 10 mg/L |
| Isoleucine | 50 mg/L |
| Yeast extract | 2 g/L |
| CaCO$_3$ | 20 g/L |

After glucose was completely consumed, the amounts of L-threonine which accumulated in the medium were determined. As a result, it was found that L-threonine production was improved in the yggG gene-amplified strain.

TABLE 2

L-threonine production

| Strain name | Concentration of L-threonine (g/L) | Yield (%) |
|---|---|---|
| B-3996 | 12.4 | 31.2 |
| B-3996/pHSG299-yggG | 14.9 | 38.6 |

[Explanation of the Sequence Listing]

SEQ ID NO: 1: nucleotide sequence of the yggG gene

SEQ ID NO: 2: amino acid sequence encoded by the yggG gene

SEQ ID NO: 3: 5'-primer for amplifying the yggG gene
SEQ ID NO: 4: 3'-primer for amplifying the yggG gene While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of producing an L-amino acid comprising culturing an L-amino acid-producing bacterium belonging to the Enterobacteriaceae family in a medium under microaerobic conditions, and collecting the L-amino acid from the medium or said bacterium, wherein said bacterium has been modified so that expression of yggG gene is enhanced as compared to a non-modified bacterium by a method selected from the group consisting of:
 a) increasing the copy number of the yggG gene,
 b) modifying an expression regulatory sequence of said gene, and
 c) combinations thereof;
wherein said yggG gene is selected from the group consisting of:
 i) a DNA comprising the nucleotide sequence of SEQ ID NO: 1, and
 ii) a DNA that hybridizes with the nucleotide sequence that is complementary to SEQ ID NO: 1, or with a probe that is prepared from said nucleotide sequence, under stringent conditions comprising washing at 0.1×SSC, 0.1% SDS, at 60° C., and wherein said DNA enhances L-amino acid producing ability of a host bacterium when it is introduced into the host bacterium.

2. The method according to claim 1, wherein the L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

3. The method according to claim 1, wherein the L-amino acid is selected from the group consisting of aromatic L-amino acids and L-threonine.

4. The method according to claim 1, wherein said yggG gene is selected from the group consisting of:
 (A) a DNA that encodes a protein comprising the amino acid sequence of SEQ ID NO: 2; and
 (B) a DNA that encodes a protein comprising the amino acid sequence of SEQ ID NO: 2, but which includes substitutions, deletions, insertions or additions of one to 10 amino acids, and wherein said DNA enhances L-amino acid producing ability of a host bacterium when it is introduced into the host bacterium.

5. The method according to claim 1, wherein said bacterium belongs to the genus *Escherichia*, *Pantoea*, or *Enterobacter*.

6. The method according to claim 1, wherein said bacterium belongs to the genus *Escherichia*.

7. The method according to claim 1, wherein said bacterium is *Escherichia coli*.

8. The method according to claim 1, wherein said microaerobic conditions comprise conditions wherein the concentration of dissolved oxygen in the culture medium is 25% or less.

9. The method according to claim 1, wherein said microaerobic conditions comprise conditions wherein oxygen transfer coefficient (Kla) in the medium is 100 or less.

* * * * *

```
                            SEQUENCE LISTING

<160> NUMBER OF SEQ ID NOS: 4

<210> SEQ ID NO 1
<211> LENGTH: 759
<212> TYPE: DNA
<213> ORGANISM: Escherichia coli
<220> FEATURE:
<221> NAME/KEY: CDS
<222> LOCATION: (1)..(756)

<400> SEQUENCE: 1 atg aaa att cgc gcc tta ttg gta gca atg agc gtg gca acg gta ctg       48
Met Lys Ile Arg Ala Leu Leu Val Ala Met Ser Val Ala Thr Val Leu
1               5                   10                  15 act ggt tgc cag aat atg gac tcc aac gga ctg ctc tca tca gga gcg       96
Thr Gly Cys Gln Asn Met Asp Ser Asn Gly Leu Leu Ser Ser Gly Ala
            20                  25                  30 gaa gct ttt cag gct tac agt ttg agt gat gcg cag gtg aaa acc ctg      144
Glu Ala Phe Gln Ala Tyr Ser Leu Ser Asp Ala Gln Val Lys Thr Leu
        35                  40                  45 agc gat cag gca tgt cag gag atg gac agc aag gcg acg att gcg cca      192
Ser Asp Gln Ala Cys Gln Glu Met Asp Ser Lys Ala Thr Ile Ala Pro
    50                  55                  60 gcc aat agc gaa tac gct aaa cgt ctg aca act att gcc aat gcg cta      240
Ala Asn Ser Glu Tyr Ala Lys Arg Leu Thr Thr Ile Ala Asn Ala Leu
65                  70                  75                  80 ggc aac aat atc aac ggt cag ccg gta aat tac aaa gtg tat atg gcg      288
Gly Asn Asn Ile Asn Gly Gln Pro Val Asn Tyr Lys Val Tyr Met Ala
                85                  90                  95 aag gat gtg aac gcc ttt gca atg gct aac ggc tgt atc cgc gtc tat      336
Lys Asp Val Asn Ala Phe Ala Met Ala Asn Gly Cys Ile Arg Val Tyr
            100                 105                 110 agc ggg ctg atg gat atg atg acg gat aac gaa gtc gaa gcg gtg atc      384
Ser Gly Leu Met Asp Met Met Thr Asp Asn Glu Val Glu Ala Val Ile
        115                 120                 125 ggt cac gaa atg ggg cac gtg gcg tta ggc cat gtg aaa aaa gga atg      432
Gly His Glu Met Gly His Val Ala Leu Gly His Val Lys Lys Gly Met
    130                 135                 140 cag gtg gca ctt ggt aca aat gcc gtg cga gta gct gcg gcc tct gcg      480
Gln Val Ala Leu Gly Thr Asn Ala Val Arg Val Ala Ala Ala Ser Ala
145                 150                 155                 160 ggc ggg att gtc gga agt tta tct caa tca caa ctt ggt aat ctg ggc      528
Gly Gly Ile Val Gly Ser Leu Ser Gln Ser Gln Leu Gly Asn Leu Gly
                165                 170                 175 gag aaa tta gtc aat tcg caa ttc tcc cag cgc cag gaa gca gaa gcc      576
Glu Lys Leu Val Asn Ser Gln Phe Ser Gln Arg Gln Glu Ala Glu Ala
            180                 185                 190 gat gat tat tct tac gat ctt ctg cgc caa cgc ggc atc agc ccg gca      624
Asp Asp Tyr Ser Tyr Asp Leu Leu Arg Gln Arg Gly Ile Ser Pro Ala
        195                 200                 205 ggt ctt gcc acc agc ttt gaa aaa ctg gca aaa ctg gaa gaa ggt cgc      672
Gly Leu Ala Thr Ser Phe Glu Lys Leu Ala Lys Leu Glu Glu Gly Arg
    210                 215                 220 caa agc tca atg ttt gac gac cat cct gca tcc gcc gaa cgc gcc cag      720
Gln Ser Ser Met Phe Asp Asp His Pro Ala Ser Ala Glu Arg Ala Gln
225                 230                 235                 240
```

```
cat att cgc gat cgc atg agc gcg gat ggg att aag taa         759
His Ile Arg Asp Arg Met Ser Ala Asp Gly Ile Lys
                245                 250
```

<210> SEQ ID NO 2
<211> LENGTH: 252
<212> TYPE: PRT
<213> ORGANISM: Escherichia coli

<400> SEQUENCE: 2

```
Met Lys Ile Arg Ala Leu Leu Val Ala Met Ser Val Ala Thr Val Leu
1               5                   10                  15

Thr Gly Cys Gln Asn Met Asp Ser Asn Gly Leu Leu Ser Ser Gly Ala
            20                  25                  30

Glu Ala Phe Gln Ala Tyr Ser Leu Ser Asp Ala Gln Val Lys Thr Leu
        35                  40                  45

Ser Asp Gln Ala Cys Gln Glu Met Asp Ser Lys Ala Thr Ile Ala Pro
50                  55                  60

Ala Asn Ser Glu Tyr Ala Lys Arg Leu Thr Thr Ile Ala Asn Ala Leu
65                  70                  75                  80

Gly Asn Asn Ile Asn Gly Gln Pro Val Asn Tyr Lys Val Tyr Met Ala
                85                  90                  95

Lys Asp Val Asn Ala Phe Ala Met Ala Asn Gly Cys Ile Arg Val Tyr
            100                 105                 110

Ser Gly Leu Met Asp Met Met Thr Asp Asn Glu Val Glu Ala Val Ile
        115                 120                 125

Gly His Glu Met Gly His Val Ala Leu Gly His Val Lys Lys Gly Met
130                 135                 140

Gln Val Ala Leu Gly Thr Asn Ala Val Arg Val Ala Ala Ser Ala
145                 150                 155                 160

Gly Gly Ile Val Gly Ser Leu Ser Gln Ser Gln Leu Gly Asn Leu Gly
                165                 170                 175

Glu Lys Leu Val Asn Ser Gln Phe Ser Gln Arg Gln Glu Ala Glu Ala
            180                 185                 190

Asp Asp Tyr Ser Tyr Asp Leu Leu Arg Gln Arg Gly Ile Ser Pro Ala
        195                 200                 205

Gly Leu Ala Thr Ser Phe Glu Lys Leu Ala Lys Leu Glu Glu Gly Arg
210                 215                 220

Gln Ser Ser Met Phe Asp Asp His Pro Ala Ser Ala Glu Arg Ala Gln
225                 230                 235                 240

His Ile Arg Asp Arg Met Ser Ala Asp Gly Ile Lys
                245                 250
```

<210> SEQ ID NO 3
<211> LENGTH: 22
<212> TYPE: DNA
<213> ORGANISM: Artificial sequence
<220> FEATURE:
<223> OTHER INFORMATION: forward primer

<400> SEQUENCE: 3

```
gctctagaga tgaaaattcg cg                                    22
```

<210> SEQ ID NO 4
<211> LENGTH: 23
<212> TYPE: DNA

```
<213> ORGANISM: Artificial sequence
<220> FEATURE:
<223> OTHER INFORMATION: reverse primer

<400> SEQUENCE: 4
cggaattctt acttaatccc atc                                           23
```